(12) United States Patent
Terada et al.

(10) Patent No.: US 9,750,257 B2
(45) Date of Patent: Sep. 5, 2017

(54) COATED SEED

(75) Inventors: Takatoshi Terada, Toyonaka (JP); Manabu Tagami, Kobe (JP); Takashi Sato, Sanda (JP); Atsushi Iwata, Takarazuka (JP); Taro Yokochi, Niihama (JP); Yasushi Kobayashi, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/141,763

(22) PCT Filed: Jan. 21, 2010

(86) PCT No.: PCT/JP2010/051067
§ 371 (c)(1),
(2), (4) Date: Jun. 23, 2011

(87) PCT Pub. No.: WO2010/087380
PCT Pub. Date: Aug. 5, 2010

(65) Prior Publication Data
US 2012/0015804 A1 Jan. 19, 2012

(30) Foreign Application Priority Data

Jan. 30, 2009 (JP) ................................. 2009-019324

(51) Int. Cl.
*A01N 25/26* (2006.01)
*A01N 51/00* (2006.01)
*A01C 1/06* (2006.01)

(52) U.S. Cl.
CPC ................ *A01N 51/00* (2013.01); *A01C 1/06* (2013.01)

(58) Field of Classification Search
CPC ........ A01N 51/00; A01N 25/00; A01N 25/08; A01N 25/10; A01C 1/06
USPC ........................................................ 504/100
See application file for complete search history.

(56) References Cited

U.S. PATENT DOCUMENTS

| | | | | |
|---|---|---|---|---|
| 3,808,740 | A * | 5/1974 | Porter et al. ................ | 47/58.1 R |
| 5,127,185 | A | 7/1992 | Kojimoto et al. | |
| 5,525,131 | A * | 6/1996 | Asano ........................... | 47/57.6 |
| 5,786,739 | A | 7/1998 | Paul et al. | |
| 2002/0134012 | A1* | 9/2002 | Ding ........................ | A01C 1/06 47/57.6 |
| 2007/0249498 | A1* | 10/2007 | Van Der Drift ............. | 504/100 |
| 2009/0041819 | A1* | 2/2009 | Tagami et al. ................ | 424/408 |
| 2010/0055143 | A1 | 3/2010 | Terada et al. | |

FOREIGN PATENT DOCUMENTS

| | | | |
|---|---|---|---|
| CN | 1964623 | A | 5/2007 |
| CN | 101146449 | A | 3/2008 |
| EP | 0187341 | A1 | 7/1986 |
| EP | 1864573 | A1 | 12/2007 |
| JP | 54-085908 | A | 7/1979 |
| JP | 8-037818 | A | 2/1996 |
| JP | 11-146707 | A | 6/1999 |
| JP | 2000236708 | A | 9/2000 |
| JP | 2005-095066 | A | 4/2005 |
| JP | 2007-119442 | A | 5/2007 |
| JP | 2008-100984 | A | 5/2008 |
| KR | 20070024580 | A | 3/2007 |
| KR | 20070118136 | A | 12/2007 |
| WO | 02080675 | A1 | 10/2002 |
| WO | 2005120226 | A2 | 12/2005 |
| WO | 2006060272 | A2 | 6/2006 |
| WO | WO 2006060272 | A2 * | 6/2006 ............. A01N 25/00 |
| WO | 2006103827 | A1 | 10/2006 |

OTHER PUBLICATIONS

Int'l Search Report issued Apr. 6, 2010 in Int'l Application No. PCT/JP2010/051067.
Office Action issued Oct. 8, 2013 in AU Application No. 2010209008.
Substantive Examination Result issued Oct. 20, 2015 in MX Application No. MX/a/2011/007236.
Office Action issued Oct. 22, 2015 in CN Application No. 201080006291.5.
Office Action issued Nov. 20, 2015 in CA Application No. 2,750,194.
English translation of an Office Action issued Oct. 1, 2013 in JP Application No. 2010-013975.
Examination Decision of the Patent Reexamination Board issued Aug. 18, 2015 in CN Application No. 201080006291.5.
Office Action issued Feb. 3, 2016 in CN Application No. 201080006291.5.
Office Action issued Jan. 28, 2016 in MX Application No. MX/a/2011/0007236.
Examiner Requisition issued Jun. 28, 2016 in JP Application No. 2010-051067.
Article 94 (3) EPC and Annex to the Communication issued Jul. 11, 2016 in EP Application No. 10735846.7.
Office Action issued Apr. 25, 2017 in KR Application No. 10-2011-7019908.

* cited by examiner

*Primary Examiner* — Janet Epps-Smith
*Assistant Examiner* — Courtney Brown
(74) *Attorney, Agent, or Firm* — Panitch Schwarze Belisario & Nadel LLP

(57) ABSTRACT

A coated seed obtained by coating a seed with a coating material containing an inorganic mineral powder and a thermosetting resin powder having an average particle diameter of 10 to 200 μm, wherein the thermosetting resin powder is a thermosetting resin powder obtained by aggregating a powdery pesticide with a thermosetting resin has an excellent quality.

16 Claims, No Drawings

COATED SEED

CROSS-REFERENCE TO RELATED APPLICATION

This application is a Section 371 of International Application No. PCT/JP2010/051067, filed Jan. 21, 2010, which was published in the Japanese language on Aug. 5, 2010, under International Publication No. WO 2010/087380 A1, and the disclosure of which is incorporated herein by reference.

TECHNICAL FIELD

The present invention relates to a coated seed containing an pesticidally active component.

BACKGROUND ART

Coated seeds are practically used for providing uniformly sowing at the mechanical sowing and improving the germination of seeds of agricultural crops.

JP-A No. 8-37818 describes an pesticide-containing coated seed obtained by mixing a coated seed and an pesticide granule. WO2006/103827 describes a granular pesticide composition obtained by fixing a powdery pesticide with a thermosetting resin.

DISCLOSURE OF THE INVENTION

The present invention provides a coated seed having an excellent performance for protecting agricultural crops by damages of diseases and pests.

The present inventors have investigated to find a coated seed having a performance for protecting agricultural crops from damages by diseases and pests. As a result, the present inventors have found that the coated seed of the present invention is suitable for protecting agricultural crops by damages of diseases and pests.

The present inventions are as described below.

[1] A coated seed obtained by coating a seed with a coating material containing an inorganic mineral powder and a thermosetting resin powder having an average particle diameter of 10 to 200 μm,
wherein the thermosetting resin powder is a thermosetting resin powder obtained by aggregating a powdery pesticide with a thermosetting resin.

[2] The coated seed according to [1], wherein the average particle diameter of the coated seed is 1 to 20 mm.

[3] The coated seed according to [1], wherein the amount of the coating material is 3 to 200 kg based on 1 kg of the seed.

[4] The coated seed according to [1] or [2], wherein the coating material is a coating material containing 10 to 99.5 wt % of an inorganic mineral powder and 0.5 to 90 wt % of a thermosetting resin powder.

[5] The coated seed according to [4], wherein the coating material is a coating material containing 5 to 30 wt % of a water repellent agent.

[6] The coated seed according to any one of [1] to [5], wherein the thermosetting resin powder is a thermosetting resin powder containing 10 to 90 wt % of a pesticidally active component.

[7] The coated seed according to [6], wherein the thermosetting resin is a urethane resin.

[8] The coated seed according to any one of [1] to [7], wherein the amount of the pesticidally active component in 1 kg of the coating seed is 5 to 200 g.

[9] The coated seed according to any one of [1] to [8], wherein the pesticidally active component is clothianidin.

[10] The coated seed according to any one of [1] to [9], wherein the seed is a seed of genus *Brassica* crops, genus *Lactuca* crops or *Solanaceous* crops.

[11] The coated seed according to any one of [1] to [9], wherein the seed is a long-shaped seed.

[12] The coated seed according to any one of [1] to [9], wherein the seed is a seed having a particle diameter of 1.0 to 4.0 mm.

The thermosetting resin powder used in the present invention is a thermosetting resin powder obtained by aggregating a powdery pesticide with a thermosetting resin.

Such a thermosetting resin powder can be produced, for example, by a method described in WO2006/103827.

Specifically, the thermosetting resin powder can be produced, for example, by the following method. A production method comprising the steps of mixing a powdery pesticide and a first liquid component as a raw material of a thermosetting resin, then adding a second liquid component as a raw material of a thermosetting resin to this mixture, reacting the first liquid component and the second liquid component to generate a thermosetting resin thereby obtaining a powdery pesticide thermosetting resin solidified material, further adding the first liquid component and the second liquid component simultaneously or sequentially to the resultant powdery pesticide thermosetting resin solidified material and reacting them to coat the powdery pesticide thermosetting resin solidified material with the thermosetting resin (hereinafter, referred to as the present thermosetting resin powder production method).

In the present invention, the powdery pesticide (hereinafter, referred to as the present powdery pesticide) has an average particle diameter (volume median diameter) of usually 1 to 100 μm, preferably 1 to 30 μm. In the present invention, the thermosetting resin powder (hereinafter, referred to as the present thermosetting resin powder) has an average particle diameter (volume median diameter) of usually 10 to 200 μm, preferably 20 to 150 μm. In the present invention, thought the present powdery pesticide may be a single pesticidally active component, it is usually a powdery composition containing a pesticidally active component and a diluent.

The average particle diameter can be measured by a laser diffraction mode particle diameter measuring instrument such as MASTERSIZER2000 manufactured by MALVERN, and the like.

In the present invention, the pesticidally active component includes commonly solid insecticidal compounds, solid fungicidal compounds, solid insect growth regulating compounds, solid plant growth regulating compounds, and the like. Examples of the pesticidally active component include compounds shown below. These are compounds which are solid at 20° C., and those which are solid at 50° C. are preferable as the pesticidally active component to be used in the present invention.

The insecticidal compounds and insect growth regulating compounds include pyrethroid compounds such as deltamethrin, tralomethrin, acrinathrin, tetramethrin, tefluthrin and the like; carbamate compounds such as propoxur, isoprocarb, xylylcarb, metolcarb, thiodicarb, XMC, carbaryl, pyrimicarb, carbofuran, methomyl, phenoxycarb, fenobcarb and the like; organophosphorus compounds such as acephate, trichlorfon, tetrachlorvinphos, dimethylvinphos, pyridafenthion, azinphos-ethyl, azinphos-methyl and the like; urea compounds such as diflubenzuron, chlorofluazuron, lufenuron, hexaflumuron, flufenoxuron, flucycloxuron, cyromazine, diafenthiuron, hexythiazox, novaluron, teflubenzuron, triflumuron, 4-chloro-2-(2-chloro-2-methyl-propyl)-5-(6-iodo-3-pyridylmethoxy)pyridazin-3(2H)-one, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea, 2-tert-butylimino-3-isopropyl-5-phenyl-3,4,5,6-tetrahydro-2H-1,3,5-thiadiazon-4-one, 1-(2,6-difluorobenzoyl)-3-[2-fluoro-4-(1,1,2,2-tetrafluoroethoxy)phenyl]urea and the like; chloronicotyl compounds such as imidacloprid, acetamiprid, clothianidin, nitenpyram, thiamethoxam, dinotefuran, thiacloprid and the like; spinosyns such as spinosad and the like; diamide compounds such as flubendiamide, chlorantraniliprole, cyantraniliprole and the like; phenylpyrazole compounds such as fipronil, ethiprole and the like; tetramic acid compounds such as spirotetramat, spiromesifen, spirodiclofen and the like; cartap, buprofezin, thiocyclam, bensultap, fenezaquin, fenpyroximate, pyridaben, hydramethylnon, chlorfenapyr, fenproxymate, pymetrozine, pyrimidifen, tebufenozide, tebufenpyrad, triazamate, indoxacarb, sulfluramid, milbemectin, ivermectin, boric acid and p-dichlorobenzene.

The fungicidal compounds include benzimidazole compounds such as benomyl, carbendazim, thiabendazol, thiophanate-methyl and the like; phenyl carbamate compounds such as diethofencarb and the like; dicarboxylmide compounds such as procymidone, iprodione, vinclozolin and the like; azole compounds such as diniconazole, probenazole, epoxyconazole, tebuconazole, difenoconazole, cyproconazole, flusilazole, triadimefon and the like; acylalanine compounds such as metalaxyl and the like; carboxamide compounds such as furametpyr, mepronil, flutolanil, trifluzamide and the like; organophosphorus compounds such as triclofos-methyl, fosetyl-aluminum, pyrazophos and the like; anilinopyrimidine compounds such as pyrimethanil, mepanipyrim, cyprodinil and the like; cyanopyrrole compounds such as fludioxonil, fenpiclonil and the like; antibiotics such as blastocidin S, kasugamycin, polyoxin, validamycin and the like; methoxyacrylate compounds such as azoxystrobin, kresoxim-methyl, SSF-126 and the like; chlorothalonil, mancozeb, captan, folpet, tricyclazole, pyroquilon, probenazole, fthalide, cymoxanil, dimethomorph, CGA245704, famoxadone, oxolinic acid, fluazinam, ferimzone, diclocymet, chlobenthiazone, isovaledione, tetrachloroisophthalonitrile, thiophthalimideoxybisphenoxyarsine, 3-iodo-2-propylbutyl carbamate, p-hydroxybenzoate, sodium dehydroacetate, potassium sorbate, orisastrobin, isotianil, tiadinil and thiuram.

The plant growth regulating compounds include maleic hydrazide, chlormequat, ethephon, gibberellin, mepiquat chloride, thidiazuron, inabenfide, paclobutrazole and uniconazole.

When the present powdery pesticide contains a diluent, the amount of the pesticidally active component in the present powdery pesticide is usually 1 to 95 wt %, preferably 10 to 90 wt % based on the amount of the present powdery pesticide, and the amount of the diluent is usually 5 to 99%, preferably 10 to 90% based on the amount of the present powdery pesticide. The diluent has an average particle diameter (volume median diameter) of usually 1 to 100 µm.

The diluent is a powdery solid carrier to be used in the pesticide powder. Examples of such a powdery solid carrier include kaolin minerals (kaolinite, dickite, nacrite, halocite and the like), serpentines (chrysotile, lizartite, antigorite, amesite and the like), montmorillonite minerals (sodium montmorillonite, calcium montmorillonite, magnesium montmorillonite and the like), smectites (saponite, hectrite, sauconite, hyderite and the like), pyrophyllite, talc, agalmatolite, micas (white mica, phengite, sericite, illite and the like), silica (cristobalite, quartz and the like), double chain structure clay minerals (palygorskite, sepiolite and the like), sulfate minerals such as gypsum and the like; dolomite, calcium carbonate, gypsum, zeolite, tuff, vermiculite, laponite, pumice, diatomaceous earth, acid clay and activated earth.

The present powdery pesticide may contain pesticide auxiliary substances such as a surfactant, stabilizer, coloring agent, perfume and the like, in addition to the pesticidally active component and the diluent.

Examples of the surfactant include nonionic surfactants such as polyoxyethylene alkyl ethers, polyoxyethylene alkylaryl ethers, polyoxyethylene lanolin alcohols, polyoxyethylene alkylphenol formalin condensates, polyoxyethylene sorbitan fatty esters, polyoxyethylene glyceryl monofatty esters, polyoxypropylene glycol monofatty esters, polyoxyethylene sorbitol fatty esters, polyoxyethylene castor oil derivatives, polyoxyethylene fatty esters, higher fatty acid glycerin esters, sorbitan fatty esters, sucrose fatty esters, polyoxyethylene polyoxypropylene block polymers, polyoxyethylene fatty amides, alkylolamides, polyoxyethylene alkylamines and the like; cationic surfactants such as alkylamine hydrochlorides such as dodecylamine hydrochloride and the like, alkyl quaternary ammonium salts such as dodecyltrimethyl ammonium salt, alkyldimethylbenzyl ammonium salt, alkylpyridinium salt, alkylisoquinolinium salt, dialkylmorpholinium salt and the like, benzethonium chloride, polyalkylvinylpyridinium salt and the like; anionic surfactants such as sodium salts of fatty acid such as sodium palmitate and the like, sodium salts of ether carboxylic acid such as sodium polyoxyethylene lauryl ether carboxylate and the like, amino acid condensates of higher fatty acids such as sodium lauroyl sarcosinate, sodium N-lauroylglutamate and the like, higher fatty ester sulfonic acid salts such as higher alkylsulfonate, lauric ester sulfonate and the like, dialkylsulfosuccinic acid salt such as dioctyl sulfosuccinate and the like, higher fatty amide sulfonic acid salts such as oleic amide sulfonate and the like, alkylarylsulfonic acid salts such as sodium dodecylbenzenesulfonate, diisopropyl-naphthalenesulfonic acid salt and the like, formalin condensates of alkylaryl sulfonic acid salts, higher alcohol sulfuric acid ester salts such as pentadecane-2-sulfate and the like, polyoxyethylene alkylphosphoric acid salts such as dipolyoxyethylene dodecyl ether phosphate and the like, styrene-maleic acid salt copolymer and the like; ampholytic surfactants such as N-laurylalanine, N,N,N-trimethylaminopropionic acid, N,N,N-trihydroxyethylaminopropionic acid, N-hexyl-N,N-dimethylaminoacetic acid, 1-(2-carboxyethyl)pyrimidinium betaine, lecithin and the like.

Examples of the stabilizer include phenol antioxidants, amine antioxidants, phosphorus type antioxidants, sulfur type antioxidants, ultraviolet absorbers; epoxidized vegetable oils such as epoxidized soybean oil, epoxidized linseed oil, epoxidized rape seed oil and the like; isopropylacid phosphate, liquid paraffin, ethylene glycol and the like.

Examples of the coloring agent include rhodamines such as rhodamine B, solar rhodamine and the like, and colorants such as Yellow No. 4, Blue No. 1, Red No. 2 and the like, and examples of the perfume include ester perfumes such as ethyl acetoacetate, ethyl enantate, ethyl cinnamate, isoamyl acetate and the like, organic acid perfumes such as caproic acid, cinnamic acid and the like, alcohol perfumes such as cinnamic alcohol, geraniol, citral, decyl alcohol and the like, aldehydes such as vanillin, piperonal, perilaldehyde and the like, ketone perfumes such as maltol, methyl β-naphthyl ketone and the like, menthol, and the like.

The present powdery pesticide is obtained by mixing pesticidally active components and if necessary a diluent, further if necessary a pesticide auxiliary substance, and pulverizing them. The present powdery pesticide can also be obtained by mixing components which have been previously pulverized into powders.

In the present invention, examples of the thermosetting resin include urethane resins, urea resins, urethane-urea resins, and epoxy resins.

The thermosetting resin is obtained in general by reacting two different kinds of liquid raw materials, and the present thermosetting resin powder can be produced, for example, by the above-described present thermosetting resin powder production method.

When the thermosetting resin is a urethane resin, one of the first liquid component and the second liquid component is a polyol, and the other is a polyisocyanate.

The polyol includes condensed polyester polyols, polyether polyols, poly(meth) acrylic acid polyols, lactone type polyester polyols, polycarbonate polyols, natural polyols and denatured products thereof and the like. The condensed polyester polyol is usually obtained by a condensation reaction of a polyol and a dibasic acid. The polyether polyol is obtained usually by addition-polymerizing propylene oxide or ethylene oxide to a polyhydric alcohol and the like. The poly(meth)acrylic acid polyol is obtained usually by a condensation reaction of poly(meth)acrylic acid and a polyol, a condensation reaction of (meth)acrylic acid and a polyol, or a polymerization reaction of a (meth)acrylate monomer. The lactone type polyester polyol is obtained by ring-opening polymerization of s-caprolactone using a polyhydric alcohol as an initiator. The polycarbonate polyol is obtained usually by reaction of a glycol and a carbonate, and the polyol includes methylene glycol, ethylene glycol, propylene glycol, tetramethylene glycol, hexamethylene diol, trimethylolpropane, polytetramethylene glycol, glycerin, pentaerythritol, sorbitol, sucrose, and oligomers thereof, and the like.

As the polyol to be used in the present invention, a mixture of a branched polyol and a linear polyol is preferable. It is preferable for the polyol mixture that the number of hydroxyl groups derived from the linear polyol is 60% or less based on the hydroxyl groups present in the polyols. The branched polyol is a polyol having three or more hydroxyl groups in the molecule, and polyols having three hydroxyl groups in the molecule are preferable. The linear polyol is a polyol having two hydroxyl groups in the molecule, and usually has a hydroxyl group on each of both ends of the molecule.

Preferable as the above-described linear polyol is a mixture of a linear polyol having an OH equivalent of 100 or less and a linear polyol having an OH equivalent of 100 or more. It is preferable for the mixture that the number of hydroxyl groups derived from the linear polyol having an OH equivalent of 100 or more is 60% or less based on the hydroxyl groups present in the polyols. The linear polyols having an OH equivalent of 100 or less include ethylene glycol, propylene glycol, and trimethylene glycol.

The polyisocyanate to be used in the present invention includes toluene diisocyanate (TDI), diphenylmethane diisocyanate (MDI), naphthalene diisocyanate, tolylene diisocyanate, hexamethylene diisocyanate, isophorone diisocyanate, xylylene diisocyanate, 4,4-methylenebis(cyclohexyl isocyanate), trimethylhexamethylene diisocyanate, 1,3-(isocyanatemethyl)cyclohexane, triphenylmethane triisocyanate, and tris(isocyanatephenyl)thiophosphate. Instead of the above-described polyisocyanates, denatured products and oligomers thereof can also be used providing that they have flowability. The denatured products include adduct denatured products, biuret denatured products, isocyanurate denatured products, block denatured products, prepolymer denatured products, dimerized denatured products, and the like. Polymethylene polyphenyl isocyanurate (polymeric MDI) obtained by condensing aniline and formalin to give a polyamine and phosgenating this is preferable from the standpoint of easiness of reaction control and low vapor pressure and excellent workability.

The urethane resin is produced by reacting a polyol and a polyisocyanate at, for example, 40 to 100° C. In this operation, catalysts such as organometals, amines and the like are added, if necessary.

Examples of the catalysts in this case include organometals such as dibutyltin diacetate, dibutyltin dichloride, dibutyltin dilaurate, dibutylthiostannic acid, stannous octylate, di-n-octyltin dilaurate and the like; triethylenediamine, N-methylmorpholine, N,N-dimethyldidodecylamine, N-dodecylmorpholine, N,N-dimethylcyclohexylamine, N-ethylmorpholine, dimethylethanolamine, N,N-dimethylbenzylamine, 1,8-diazabicyclo(5.4.0)undecene-7, isopropyl titanate, tetrabutyltitanate, oxyisopropyl vanadate, n-propyl zirconate, and 1,4-diazabicyclo[2.2.2]octane.

When the thermosetting resin is a urea resin, one of the first liquid component and the second liquid component is a polyamine, and the other is a polyisocyanate.

The polyisocyanate includes, for example, the above-described polyisocyantes.

The polyamine includes, for example, diethylenetriamine and triethylenetetramine.

When the thermosetting resin is a urethane-urea resin, one of the first liquid component and the second liquid component is a polyol and a polyamine, and the other is a polyisocyanate.

When the thermosetting resin is an epoxy resin, one of the first liquid component and the second liquid component is a hardening agent, and the other is a compound having a glycidyl group.

The hardening agent is usually a polyamine. Examples of the compound having a glycidyl group include polyglycidyl ether and polyglycidylamine.

Examples of the polyamine include diethylenetriamine, triethylenetetramine, metaxylylenediamine, isophoronediamine, methyliminobispropylamine, mencenediamine, metaphenylenediamine, diaminophenylmethane, diaminodiphenylsulfone, diaminodiethyldiphenylmethane, polyamide-denatured polyamine, ketone-denatured polyamine, epoxy-denatured polyamine, thiourea-denatured polyamine, Mannich-denatured polyamine and Michael addition-denatured polyamine.

The compound having a glycidyl group includes polyglycidyl ethers such as bisphenol A type polyglycidyl ether, bisphenol F type polyglycidyl ether, hydrogenated bisphenol A type polyglycidyl ether, naphthalene type polyglycidyl ether, brominated bisphenol A type polyglycidyl ether, bisphenol S type polyglycidyl ether, bisphenol AF type polyglycidyl ether, biphenyl type polyglycidyl ether, fluolein type polyglycidyl ether, phenol novolak type polyglycidyl ether, o-cresol novolak type polyglycidyl ether, DPP novolak type polyglycidyl ether, trishydroxyphenylmethane type polyglycidyl ether, tetraphenylolethane type polyglycidyl ether and the like; polyglycidylamines such as tetraglycidyldiaminodiphenylmethane type polyglycidylamine, hydantoin type polyglycidylamine, 1,3-bis(N,N-diglycidylaminomethyl)cyclohexane, aniline type polyglycidylamine, toluidine type polyglycidylamine, triglycidyl isocyanurate type polyglycidylamine, aminophenol type polyglycidylamine, and the like.

When the thermosetting resin is a urethane resin, the viscosity of the polyol is preferably 1000 mPa·s or less, further preferably 800 mPa·s or less (B type viscometer, 25° C., 12 revolutions). The viscosity of the polyisocyanate is preferably 300 mPa·s or less, further preferably 200 mPa·s or less (B type viscometer, 25° C., 12 revolutions).

The step of mixing the present powdery pesticide and the first liquid component as a raw material of a thermosetting resin is generally carried out by adding the first liquid component to a vessel while rolling the present powdery pesticide in the vessel under dry conditions wherein the powdery pesticide is not dispersed in the liquid medium.

The step is carried out usually at 0 to 100° C., preferably at 20 to 90° C. From the standpoint of safety, the step is carried out preferably under a nitrogen atmosphere.

As the method of rolling the present powder pesticide in a vessel, mentioned are, for example, a) a method in which a vessel of pan type or drum type containing the present powdery pesticide is rotated around an inclined or horizontal axis, b) a method in which, in a vessel containing the present powdery pesticide, a stirring blade of approximately the same size as the diameter of the bottom part of the vessel is placed and this is rotated, and c) a method in which, in a vessel containing the present powdery pesticide, the present powdery pesticide is rolled by air flow.

The subsequent step of adding to this the second liquid component as a raw material for a thermosetting resin is carried out usually at 0 to 100° C., preferably at 20 to 90° C. From the standpoint of safety, the step is carried out preferably under a nitrogen atmosphere.

The second liquid component is used in a proportion of usually 0.9 to 1.05 equivalents, preferably 0.95 to 1.00 equivalents based on one equivalent of the first liquid component.

If the thermosetting resin is a urethane resin and the first liquid component is a polyol, then, the second liquid component is a polyisocyanate, and it is advantageous to appropriately adjust the amount of the polyisocyanate so that the amount of the polyisocyanate based on an isocyanate group is 0.8 to 1.1 equivalents, preferably 0.9 to 1.1 equivalents, further preferably 0.95 to 1.05 equivalents based on one equivalent of the polyol based on a hydroxyl group.

The step of reacting the first liquid component and the second liquid component to generate a thermosetting resin is carried out usually at 0 to 100° C., preferably at 20 to 95° C., further preferably at 40 to 90° C. From the standpoint of safety, the step is carried out preferably under a nitrogen atmosphere. In this process, it is preferable to carry out mixing while imparting shear force by a rotating blade to the powdery pesticide.

Specifically mentioned is a method of stirring the present powdery pesticide by a blade rotating at a rate of 50 to 3000 m/min, preferably 100 to 2000 m/min, further preferably 200 to 1000 m/min in terms of the speed of the leading edge of the blade. The stirring is usually carried out until an un-hardened thermosetting resin is hardened completely and the resultant powdery pesticide thermosetting resin solidified material shows no stickiness.

This time varies depending on the property of the thermosetting resin and the operation temperature.

To the powdery pesticide thermosetting resin solidified material obtained as described above, further, the first liquid component and the second liquid component are added simultaneously or sequentially, and these are reacted to generate a thermosetting resin, and this process can be carried out once or repeated several times to increase the thickness of a coat made of the thermosetting resin, thereby retarding release of a pesticidally active component.

The amount of an un-hardened thermosetting resin to be added, namely, the total amount of the first liquid component and the second liquid component is usually 10 to 300 parts by weight, preferably 20 to 200 parts by weight, more preferably 50 to 150 parts by weight based on 100 parts by weight of the present powdery pesticide.

As the specific vessel to be used in the present thermosetting resin powder production method, there are mentioned New-Gra Machine manufactured by Seishin Enterprise Co., Ltd. as an apparatus in which particles manifest circular motion in the vessel along the outer periphery thereof, and High Speed Mixer and High Flex Gral manufactured by Fukae Powtec Corp. as an apparatus equipped with an agitator of low revolution in a mixer and a chopper of high revolution on a side face thereof, in which charged raw materials are mixed, dispersed and sheared in a short period of time by the action of both the blades. Further, High Speed Mixer manufactured by Freund Corporation, Vertical Granulator manufactured by Powrex Corporation, and New Speed Mill manufactured by Okada Seiko Co., Ltd. are mentioned as apparatuses showing the same performance.

For example, an apparatus described in JP-A No. 9-75703 is specifically mentioned.

In the present thermosetting resin powder, the amount of the thermosetting resin is usually 10 to 300 parts by weight, preferably 20 to 200 parts by weight, further preferably 50 to 150 parts by weight bases on 100 parts by weight of the present powdery pesticide.

As the inorganic mineral powder to be used in the present invention, use is made of inorganic mineral powders used in the field of usual coated seeds. Examples of the inorganic mineral powder include kaolin minerals (kaolinite, dickite, nacrite, halocite and the like), serpentines (chrysotile, lizartite, antigorite, amesite and the like), montmorillonite minerals (sodium montmorillonite, calcium montmorillonite, magnesium montmorillonite and the like), smectites (saponite, hectrite, sauconite, hyderite and the like), pyrophyllite, talc, agalmatolite, micas (white mica, phengite, sericite, illite and the like), silica (cristobalite, quartz and the like), double chain structure clay minerals (palygorskite, sepiolite and the like), sulfate minerals such as gypsum and the like; dolomite, calcium carbonate, gypsum, zeolite, boiling stone, tuff, vermiculite, laponite, pumice, diatomaceous earth, acid clay and activated earth. As the inorganic mineral powder, those containing a composite chain structure clay mineral as a component are preferable. The proportion of the inorganic mineral powder is preferably 5 to 90 wt %, further preferably 10 to 70 wt % based on the total amount of coating materials. The inorganic mineral powder used in the present invention has an average particle diameter (volume median diameter) of usually 1 to 100 μm, preferably 5 to 50 μm. The average particle diameter can be measured by Laser Diffraction Particle Size Distribution Analyzer (HORIBA LA-300, manufactured by Horiba Ltd.).

The coating material may contain auxiliary substances to be used in coated seeds such as a binder, water repellent agent and the like, in addition to the inorganic mineral powder and the thermosetting resin powder having an average particle diameter of 10 to 200 μm.

Examples of the water repellent agent include oils and fats, waxes, higher fatty acids and metal salts of higher fatty acids, higher aliphatic alcohols and alkylene oxide adducts of higher aliphatic alcohols, silicon type water repellent agents, and fluorine type water repellent agents. As the water repellent agent, higher fatty acids and metal salts of higher fatty acids are preferable, further, di-valent metal salts of higher fatty acids are more preferable, and calcium stearate is particularly preferable.

Examples of the binder include water-soluble polymers such as polyvinyl alcohol, polyvinylpyrrolidone, carboxymethylcellulose, starch, sucrose, cellulose acetate, cellulose acetate propionate, methylcellulose, hydroxypropylcellulose, pullulan, gelatin and the like; and, aqueous emulsions such as a vinyl acetate emulsion, acryl emulsion, urethane emulsion and the like.

As the seed to be used in the coated seed of the present invention, for example, seeds having an average particle diameter of 1.0 to 4.0 mm are mentioned. Examples of the seed shape include the following shapes.

(i) long-shaped seeds having a length of 2.0 to 5.0 mm, a width of 0.5 to 2.0 mm, and a thickness of 0.3 to 0.5 mm (for example, lettuce seeds)

(ii) approximate spherical seeds having a diameter of 1.0 to 3.0 mm (for example, cabbage seeds)

(iii) flat oval seeds having a diameter of 1.5 to 4.0 mm (for example, eggplant seeds)

Particularly, examples thereof include vegetable seeds, flowering grass seeds, pasture grass seeds, cereal seeds and industrial crop seeds, more specifically, those listed below.

The vegetable seeds include seeds of cucurbitaceous vegetables such as for example cucumber, melon, pumpkin and the like, seeds of *solanaceous* vegetables such as for example eggplant, tomato and the like, seeds of papilionaceous vegetables such as for example pea, common bean and the like, seeds of liliaceae vegetables such as for example onion, Welsh onion and the like, seeds of genus *Brassica* such as for example turnip, nappa cabbage, cabbage, broccoli, cauliflower and the like and brassicaceae vegetables such as radish and the like, seeds of umbelliferous vegetables such as for example carrot, celery and the like, seeds of asteraceous vegetables such as for example burdock, lettuce, crown daisy and the like, seeds of labiatae vegetables such as for example Japanese basil and the like, seeds of chenopodiaceous vegetables such as for example spinach and the like; etc.

The flowering grass seeds include seeds of brassicaceous flowering grasses such as for example ornamental cabbage, stock, alyssum and the like, seeds of campanulaceous flowering grasses such as for example lobelia and the like, seeds of asteraceous flowering grasses such as for example aster, zinnia, sunflower and the like, seeds of ranunculaceous flowering grasses such as for example delphinium and the like, seeds of Scrophulariaceous flowering grasses such as for example snapdragon and the like, seeds of primulaceous flowering grasses such as for example primula and the like, seeds of begoniaceous flowering grasses such as for example begonia and the like, seeds of labiatae flowering grasses such as for example salvia and the like, seeds of violaceous flowering grasses such as for example pansy, viola and the like, seeds of *solanaceous* flowering grasses such as for example petunia and the like, seeds of gentian flowering grasses such as for example eustoma and the like; etc.

The pasture grass seeds include seeds of pasture grasses such as for example timothy (*Phleum pratense*), Italian ryegrass (*Lolium multiflorum* Lam.), bermuda grass (*Cynodon dactylon*), oatshay (oat), sudan grass, cram grass, fescue, and orchard grass (*Dactylis glomerata*).

The cereal seeds include, for example, rice, barley, wheat, soybean, millet, Japanese millet and proso millet.

The industrial crop seeds include, for example, seeds of Chenopodiaceae such as sugar beat and the like, seeds of Solanaceae such as tobacco and the like, seeds of Brassicaceae such as rapeseed and the like, and seeds of Gramineae such as rush and the like.

The seeds applicable as the coated seed in the present invention include also seeds of plants having resistance to an HPPD inhibitor such as isoxaflutole, an ALS inhibitor such as imazethapyr, thifensulfuron-methyl or the like, an EPSP synthesizing enzyme inhibitor such as glyphosate or the like, a glutamine synthesizing enzyme inhibitor such as glufosinate or the like, an acetyl CoA carboxylase inhibitor such as sethoxydim or the like, or an herbicide such as bromoxynil, dicamba, 2,4-D or the like, which resistance has been imparted by a classical breeding method or a genetic engineering technique.

Examples of the plant having the resistance imparted by a classical breeding method include rapeseed, wheat, sunflower and rice having resistance to imidazolinone ALS inhibiting type herbicides such as imazethapyr or the like, which are already marketed under the trade name of Clearfield (registered trademark). Likewise, examples thereof include soybean having resistance to sulfonylurea ALS inhibiting type herbicides such as thifensulfuron-methyl or the like imparted by a classical breeding method, which is already marketed under the trade name of STS soybean. Likewise, examples thereof include SR corn and the like having resistance to acetyl CoA carboxylase inhibitors such as trione oxime herbicides and aryloxyphenoxypropionic acid herbicides and the like imparted by a classical breeding method. Plants having imparted resistance to acetyl CoA carboxylase inhibitors are described in Proceedings of the National Academy of Sciences of the United States of America (Proc. Natl. Acad. Sci. USA), vol. 87, p. 7175-7179 (1990), and the like.

In addition, a mutant acetyl CoA carboxylase which is resistant to an acetyl CoA carboxylase inhibitor is described in Weed Science, vol. 53, p. 728-746 (2005), and the like, and a plant resistant to an acetyl CoA carboxylase inhibitor can be produced by introducing such a mutant acetyl CoA carboxylase gene into a plant by a genetic engineering technique or introducing a mutation correlated with resistance imparting into a plant acetyl CoA carboxylase.

Further, nucleic acids for introduction of a base substitution mutation can be introduced into the cells of a plant by a technology typified by chimeraplasty (see, Gura T. 1999, Repairing the Genome's Spelling Mistakes, Science 285: 316-318) to induce a site-directed amino acid substitution mutation in an acetyl CoA carboxylase gene, an ALS gene or the like of the plant, and thereby a plant resistant to an acetyl CoA carboxylase inhibitor, and ALS inhibitor and the like can be produced.

Examples of the plant having the resistance imparted by a genetic engineering technique include corn, soybean, cotton, rapeseed and sugar beet cultivars which are resistant to glyphosate, which are already marketed under the trade names of RoundupReady (registered trademark), AgrisureGT, and the like. Likewise, examples thereof include corn, soybean, cotton and rapeseed cultivars which has resistance to glufosinate imparted by a genetic engineering technique, which are already marketed under the trade name of LibertyLink (registered trademark) and the like. Likewise, cotton having resistance to bromoxynil imparted by a genetic engineering technique is already marketed under the trade name of BXN.

The seeds applicable as the coated seed in the present invention include also seeds of plants which have got an ability of synthesizing selective toxins known for example as genus *Bacillus* and the like, using a gene engineering technique. Toxins to be expressed in such genetically modified plants include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1, Cry9C or the like; insecticidal proteins such as VIP 1, VIP 2, VIP 3, VIP 3A and the like; insecticidal proteins derived from nematodes; toxins produced by animals such as scorpion toxins, spider toxins, bee toxins or insect-specific nerve toxins and the like; fungal toxins; plant lectin; agglutinin; protease inhibitors such as trypsin inhibitors, serine protease inhibitors, patatin, cystatin, papain inhibitors and the like; ribosome-inactivating proteins (RIP) such as ricin, corn-RIP, abrin, rufin, saporin, briodin and the like; steroid metabolizing enzymes such as 3-hydroxysteroid oxidase, ecdysteroid-UDP-glucosyltransferase, cholesterol oxidase and the like; ecdysone inhibitors; HMG-CoA reductase; ion channel inhibitors such as sodium channel inhibitors, calcium channel inhibitors and the like; juvenile hormone esterase; diuretic hormone receptors; stilbene synthase; bibenzyl synthase; chitinase; glucanase; etc.

The toxins to be expressed in such genetically modified plants include also hybrid toxins of the insecticidal proteins such as δ-endotoxins such as Cry1Ab, Cry1Ac, Cry1F, Cry1Fa2, Cry2Ab, Cry3A, Cry3Bb1, Cry9C, Cry34Abm Cry35Ab or the like and insecticidal proteins such as VIP 1, VIP 2, VIP 3, VIP 3A or the like; partially deleted toxins thereof; and modified toxins thereof. The hybrid toxin is made by a new combination of different domains of these proteins, using a genetic engineering technique. As the partially deleted toxin, Cry1Ab in which a part of an amino acid sequence is deleted is known. In the modified toxin, one or more of amino acids of a naturally occurring toxin are substituted.

Examples of these toxins and genetically modified plants having an ability to produce these toxins are described in EP-A-0 374 753, WO 93/07278, WO 95/34656, EP-A-0 427 529, EP-A-451878, WO 03/052073, and the like.

The toxins contained in these genetically modified plants impart resistance, particularly, to coleopteran pests, hemipteran pests, dipteran pests, lepidopteran pests and nematodes, to a plant.

The genetically modified plants which contain one or more insecticidal pest-resistant genes and express one or more toxins are already known, and some of them are commercially available. Examples of such genetically modified plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Herculex I (registered trademark) (a corn cultivar expressing Cry1Fa2 toxin and phosphinothricin N-acetyltransferase (PAT) for imparting resistance to gluphosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (GA21 glyphosate-resistance character), Agrisure CB Advantage (Bt11 corn borer (CB) character), Protecta (registered trademark), and the like.

The seeds applicable as the coated seed in the present invention include also seeds of plants endowed with an ability of producing an anti-pathogenic substance having a selective action, using a gene engineering technique.

As examples of the anti-pathogen substance, PR proteins and the like are known (PRPs described in EP-A-0392225). Such anti-pathogen substances and genetically modified plants which produce the anti-pathogen substances are described in EP-A-0392225, WO 95/33818, EP-A-0353191, and the like.

Examples of the anti-pathogen substance to be expressed in such genetically modified plants include ion channel inhibitors such as sodium channel inhibitors, calcium channel inhibitors (KP1, KP4, KP6 toxins etc. produced by viruses are known) and the like; stilbene synthase; bibenzyl synthase; chitinase; glucanase; PR proteins; anti-pathogen substances produced by microorganisms such as peptide antibiotics, heterocycle-containing antibiotics, protein factors involved in plant disease-resistance (called plant disease resistant gene, and described in WO 03/000906); and the like. Such anti-pathogen substances and genetically modified plants which produce the anti-pathogen substances are described in EP-A-0392225, WO 95/33818, EP-A-0353191, and the like.

The seeds applicable as the coated seed in the present invention include also seeds of plants adding characters such as a modified oil component and reinforcement of amino acid content which have been imparted by a genetically modified technique. Examples thereof include VISTIVE™ (low linolenic soybean which has a reduced content of linolenic acid), high-lysine (high-oil) corn (corn which has an increased content of lysine or oil), and the like.

Furthermore, the plants include also stacked cultivars combining of two or more of beneficial characters such as the above-described classical herbicide character or herbicide-resistant gene, an insecticidal pest-resistant gene, an anti-pathogen substance-producing gene, a modified oil component, and reinforcement of amino acid content, and the like.

The coated seed of the present invention can be produced, for example, by coating a seed with a coating material containing an inorganic mineral carrier and a thermosetting resin powder having an average particle diameter of 10 to 200 μm. The coating material contains an inorganic mineral carrier and a thermosetting resin powder having an average particle diameter of 10 to 200 μm, and if necessary, auxiliary substances such as a binder, water repellent agent and the like. The coating material is obtained by mixing these constituent components. The coating method includes also a method in which water is added to the coating material and mixed, and seeds are coated with the mixture, before drying.

Examples of the seed coating method include a dry granulation method, fluidized bed granulation method and wet granulation method. The granulator to be used for coating includes, for example, an inclined rotation pan shaped granulator and a fluidized bed granulator.

In the wet granulation method, coated seeds containing moisture are obtained. The coated seeds containing moisture are usually dried for preservation. Drying of the coated seeds containing moisture is carried out usually at 50° C. or lower, preferably at 25° C. or higher and 50° C. or lower.

When the granulation method is wet granulation, the water content of inner seeds in the coated seeds of the present invention obtained by drying is suitably 9 w/w % or less, more suitably 6.5 w/w % or less.

The amount of the inorganic mineral powder contained in the coating material, in the present invention, is usually 10 to 99.5 wt %, preferably 30 to 80 wt % based on the total amount of the coating material. In the present invention, the amount of the thermosetting resin powder having an average particle diameter of 10 to 200 μm contained in the coating material is usually 0.5 to 90 wt %, preferably 2 to 40 wt %. In the present invention, the amount of the water repellent agent contained in the coating material is usually 0 to 30 wt %, preferably 5 to 30 wt %, further preferably 10 to 25 wt % based on the total amount of the coating material.

In the coated seed of the present invention, the coating material is used in an amount of usually 3 to 200 kg based on 1 kg of the seeds.

The total amount of pesticidally active components contained in the coated seed of the present invention is usually 5 to 200 g per 1 kg of the coated seeds.

The coated seed of the present invention has an average particle diameter (volume median diameter) of, for example, 1 to 20 mm. Specifically, for seeds of vegetables such as cabbage, lettuce, nappa cabbage, carrot and the like, spherical or approximate spherical seeds having a diameter of 2.5 to 3.5 mm are applied; for large size seeds of vegetables such as onion, Welsh onion, tomato, eggplant and the like, spherical or approximate spherical seeds having a diameter of 3.5 to 4.5 mm are applied; and for small size seeds of vegetables such as eustoma and the like, spherical or approximate spherical seeds having a diameter of 1.0 to 1.7 mm are applied.

The coated seed of the present invention is capable of protecting agricultural crops from damages of diseases and insects with causing little chemical injury on the crops, by a usual method of using coated seeds.

EXAMPLES

The present invention will be illustrated more specifically by examples such as production examples, test examples and the like, but the present invention is not limited only to these examples.

Reference Example 1

Seventy (70.0) parts by weight of (E)-1-(2-chloro-1,3-thiazol-5-ylmethyl)-3-methyl-2-nitroguanidine (common name: clothianidin) and 30.0 parts by weight of pyrophyllite (Shokozan Clay S, manufactured by Shokozan Mining Co., Ltd.) were mixed. This mixture was pulverized by a centrifugal pulverizer to obtain a powdery pesticide having an average particle diameter (volume median diameter) (MASTERSIZER 2000 manufactured by MALVERN) of 10.0 μm (hereinafter, referred to as the present powdery pesticide 1).

A mixture of 46.3 parts by weight of SUMIPHEN™ (branched polyether polyol, manufactured by Sumika Bayer Urethane), 52.2 parts by weight of SUMIPHEN 1600U (linear polyether polyol, manufactured by Sumika Bayer Urethane) and 1.5 parts by weight of 2,4,6-tris(dimethylaminomethyl)phenol was obtained (hereinafter, referred to as polyol premix 1). This polyol premix 1 had a viscosity of 322 m·Pa (B type viscometer, 25° C., 12 revolution, rotor No. 1).

Reference Example 2-1

Into a vessel of High Speed Mixer apparatus (FS-GS-25 type manufactured by Fukae Powtec Corp.; an apparatus having an agitator blade rotating around a vertical line as the axis passing through the center of the bottom surface of a round dish-shaped vessel part and a chopper blade rotating around a horizontal line as the axis penetrating the side surface of a round dish-shaped vessel part), 100 parts by weight of the present powdery pesticide 1 was charged. The agitator blade (revolution: 382 rpm) and the chopper blade (revolution: 3500 rpm) of the apparatus were rotated. When the temperature of the present powdery pesticide 1 was 85±5° C., 1.93 parts by weight of the polyol premix 1 was added over a period of 2 minutes to the present powdery pesticide 1. Three minutes after completion of addition of the present polyol premix 1, 1.07 parts by weight of SUMIDUR 44V10 (polymethylene polyphenyl polyisocyanate, viscosity 130 m·Pa (25° C.), manufactured by Sumika Bayer Urethane) was added over a period of 2 minutes at 85±5° C. Six minutes after completion of addition of Sumidule 44V10, the following operation (hereinafter, referred to as urethane addition operation) was repeated nine times at 85±5° C.

[Urethane Addition Operation]

Adding 1.93 parts by weight of the polyol premix 1 over a period of 2 minutes while stirring→keeping the stirring condition for 3 minutes→adding 1.07 parts by weight of Sumidule 44V10 over a period of 2 minutes while stirring→keeping the stirring condition for 6 minutes Then, 4.76 parts by weight of calcium carbonate was added, and the mixture was stirred for 3 minutes to obtain a thermosetting resin powder (hereinafter, referred to as the present thermosetting resin powder 1; volume median diameter: 35 μm, apparent specific gravity: 0.36 g/ml).

Reference Example 2-2

The same operation as in Reference Example 2-1 was carried out, excepting that the urethane addition operation was repeated 20 times, to obtain a thermosetting resin powder (hereinafter, referred to as the present thermosetting resin powder 2; urethane resin raw material total addition amount based on 100 parts by weight of the present powdery pesticide 1:60 parts by weight, volume median diameter: 41 μm, apparent specific gravity: 0.40 g/ml).

Reference Example 2-3

The same operation as in Reference Example 2-1 was carried out, excepting that the urethane addition operation was repeated 30 times, to obtain a thermosetting resin powder (hereinafter, referred to as the present thermosetting resin powder 3; urethane resin raw material total addition amount based on 100 parts by weight of the present powdery pesticide 1:90 parts by weight, volume median diameter: 44 μm, apparent specific gravity: 0.42 g/ml).

Reference Example 2-4

The same operation as in Reference Example 2-1 was carried out, excepting that the urethane addition operation was repeated 45 times, to obtain a thermosetting resin powder (hereinafter, referred to as the present thermosetting resin powder 4; urethane resin raw material total addition amount based on 100 parts by weight of the present powdery pesticide 1:135 parts by weight, volume median diameter: 46 μm, apparent specific gravity: 0.45 g/ml).

Reference Example 2-5

The same operation as in Reference Example 2-1 was carried out, excepting that the urethane addition operation was repeated 58 times, to obtain a thermosetting resin powder (hereinafter, referred to as the present thermosetting resin powder 5; urethane resin raw material total addition amount based on 100 parts by weight of the present powdery pesticide 1:174 parts by weight, volume median diameter: 47 μm, apparent specific gravity: 0.51 g/ml).

Production Example 1

Thirty three (33) parts by weight of diatomaceous earth, 30 parts by weight of pyrophyllite, 11 parts by weight of sepiolite, 20 parts by weight of calcium stearate and 6 parts by weight of the present thermosetting resin powder 1 were mixed. This mixture was stirred for 30 minutes to obtain a coating material (hereinafter, referred to as the present coating material 1).

Cabbage seeds (63 g, number of seeds: about 20000) were rolled in a rolling granulator of centrifugal flow mode having a diameter of 36 cm. While spraying tap water onto the rolling seeds, 340 g of the present coating material 1 was gradually added. In this operation, the cabbage seeds were coated with the present coating material 1. Air of 25° C. was blown for 30 minutes to the seeds coated with the present coating material 1, further, the seeds were dried overnight in a drying machine of 35° C., to obtain coated seeds having an average particle diameter of 3.0 mm (hereinafter, referred to as the present coated seed 1).

The amount of clothianidin contained in the present coated seed 1 was 25 g per 1 kg of the coated seeds Production Example 2

Thirty one (31) parts by weight of diatomaceous earth, 27 parts by weight of pyrophyllite, 10 parts by weight of sepiolite, 20 parts by weight of calcium stearate and 12 parts by weight of the present thermosetting resin powder 1 were mixed. This mixture was stirred for 30 minutes to obtain a coating material (hereinafter, referred to as the present coating material 2).

The same operation as in Production Example 1 was carried out, excepting that the present coating material 2 was used instead of the present coating material 1, to obtain coated seeds having an average particle diameter of 3.0 mm (hereinafter, referred to as the present coated seed 2).

The amount of clothianidin contained in the present coated seed 2 is 50 g per 1 kg of the coated seeds.

Production Example 3

Thirty two (32) parts by weight of diatomaceous earth, 29 parts by weight of pyrophyllite, 11 parts by weight of sepiolite, 20 parts by weight of calcium stearate and 8 parts by weight of the present thermosetting resin powder 2 were mixed. This mixture was stirred for 30 minutes to obtain a coating material (hereinafter, referred to as the present coating material 3).

The same operation as in Production Example 1 was carried out, excepting that the present coating material 3 was used instead of the present coating material 1, to obtain coated seeds having an average particle diameter of 3.0 mm (hereinafter, referred to as the present coated seed 3).

The amount of clothianidin contained in the present coated seed 3 is 25 g per 1 kg of the coated seeds.

Production Example 4

Twenty nine (29) parts by weight of diatomaceous earth, 25 parts by weight of pyrophyllite, 10 parts by weight of sepiolite, 20 parts by weight of calcium stearate and 16 parts by weight of the present thermosetting resin powder 2 were mixed. This mixture was stirred for 30 minutes to obtain a coating material (hereinafter, referred to as the present coating material 4).

The same operation as in Production Example 1 was carried out, excepting that the present coating material 4 was used instead of the present coating material 1, to obtain coated seeds having an average particle diameter of 3.0 mm (hereinafter, referred to as the present coated seed 4).

The amount of clothianidin contained in the present coated seed 4 is 25 g per 1 kg of the coated seeds.

Production Example 5

Cabbage seeds (63 g, number of seeds: about 20000) were rolled in a rolling granulator of centrifugal flow mode having a diameter of 36 cm. While spraying tap water onto the rolling seeds, 340 g of the present coating material 4 was gradually added. In this operation, the cabbage seeds were coated with the present coating material 4. Air of 25° C. was blown for 30 minutes to the seeds coated with the present coating material 4, further, the seeds were dried overnight in a drying machine of 35° C. to obtain coated seeds having an average particle diameter of 3.0 mm (hereinafter, referred to as the present coated seed 5).

The amount of clothianidin contained in the present coated seed 5 is 50 g per 1 kg of the coated seeds.

Production Example 6

Twenty nine (29) parts by weight of diatomaceous earth, 25 parts by weight of pyrophyllite, 10 parts by weight of sepiolite, 20 parts by weight of calcium stearate, 16 parts by weight of the present thermosetting resin powder 2 and 0.071 parts by weight of thiuram wettable powder (trade name: Sankyo Thiuram 80; manufactured by Hokkai Sankyo Co., Ltd.) were mixed. This mixture was stirred for 30 minutes to obtain a coating material (hereinafter, referred to as the present coating material 6).

The same operation as in Production Example 5 was carried out, excepting that the present coating material 6 was used instead of the present coating material 4, to obtain coated seeds having an average particle diameter of 3.0 mm (hereinafter, referred to as the present coated seed 6).

The amount of clothianidin contained in the present coated seed 6 is 50 g per 1 kg of the coated seeds.

Production Example 7

Thirty two (32) parts by weight of diatomaceous earth, 28 parts by weight of pyrophyllite, 11 parts by weight of sepiolite, 20 parts by weight of calcium stearate and 9 parts by weight of the present thermosetting resin powder 3 were mixed. This mixture was mixed for 30 minutes to obtain a coating material (hereinafter, referred to as the present coating material 7).

The same operation as in Production Example 1 was carried out, excepting that the present coating material 7 was used instead of the present coating material 1, to obtain coated seeds having an average particle diameter of 3.0 mm (hereinafter, referred to as the present coated seed 7).

The amount of clothianidin contained in the present coated seed 7 is 25 g per 1 kg of the coated seeds.

Production Example 8

Twenty eight (28) parts by weight of diatomaceous earth, 25 parts by weight of pyrophyllite, 9 parts by weight of sepiolite, 20 parts by weight of calcium stearate and 18 parts by weight of the present thermosetting resin powder 3 were mixed. This mixture was stirred for 30 minutes to obtain a coating material (hereinafter, referred to as the present coating material 8).

The same operation as in Production Example 1 was carried out, excepting that the present coating material 8 was used instead of the present coating material 1, to obtain coated seeds having an average particle diameter of 3.0 mm (hereinafter, referred to as the present coated seed 8).

The amount of clothianidin contained in the present coated seed 8 is 50 g per 1 kg of the coated seeds.

Production Example 9

The same operation as in Production Example 5 was carried out, excepting that the present coating material 8 was used instead of the present coating material 4, to obtain coated seeds having an average particle diameter of 3.0 mm (hereinafter, referred to as the present coated seed 9).

The amount of clothianidin contained in the present coated seed 9 is 50 g per 1 kg of the coated seeds.

Production Example 10

Twenty weight (28) parts by weight of diatomaceous earth, 25 parts by weight of pyrophyllite, 9 parts by weight of sepiolite, 20 parts by weight of calcium stearate, 18 parts by weight of the present thermosetting resin powder 3 and 0.071 parts by weight of thiuram wettable powder (trade name: Sankyo Thiuram 80; manufactured by Hokkai Sankyo Co., Ltd.) were mixed. This mixture was stirred for 30 minutes to obtain a coating material (hereinafter, referred to as the present coating material 10).

The same operation as in Production Example 5 was carried out, excepting that the present coating material 10 was used instead of the present coating material 4, to obtain coated seeds having an average particle diameter of 3.0 mm (hereinafter, referred to as the present coated seed 10).

The amount of clothianidin contained in the present coated seed 10 is 50 g per 1 kg of the coated seeds.

Production Example 11

Twenty six (26) parts by weight of diatomaceous earth, 23 parts by weight of pyrophyllite, 9 parts by weight of sepiolite, 20 parts by weight of calcium stearate and 22 parts by weight of the present thermosetting resin powder 4 were mixed. This mixture was stirred for 30 minutes to obtain a coating material (hereinafter, referred to as the present coating material 11).

The same operation as in Production Example 5 was carried out, excepting that the present coating material 11 was used instead of the present coating material 4, to obtain coated seeds having an average particle diameter of 3.0 mm (hereinafter, referred to as the present coated seed 11).

The amount of clothianidin contained in the present coated seed 11 is 50 g per 1 kg of the coated seeds.

Production Example 12

Twenty four (24) parts by weight of diatomaceous earth, 22 parts by weight of pyrophyllite, 8 parts by weight of sepiolite, 20 parts by weight of calcium stearate and 26 parts by weight of the present thermosetting resin powder 5 were mixed. This mixture was stirred for 30 minutes to obtain a coating material (hereinafter, referred to as the present coating material 12).

The same operation as in Production Example 5 was carried out, excepting that the present coating material 12 was used instead of the present coating material 4, to obtain coated seeds having an average particle diameter of 3.0 mm (hereinafter, referred to as the present coated seed 12).

The amount of clothianidin contained in the present coated seed 12 is 50 g per 1 kg of the coated seeds.

Production Example 13

Fifty five (55) parts by weight of palygorskite, 18 parts by weight of calcium stearate and 27 parts by weight of the present thermosetting resin powder 2 were mixed. This mixture was stirred for 30 minutes to obtain a coating material (hereinafter, referred to as the present coating material 13).

Lettuce seeds (50 g, number of seeds: about 37000) were rolled in a rolling granulator of centrifugal flow mode having a diameter of 36 cm. While spraying tap water onto the rolling seeds, 800 g of the present coating material 13 was gradually added. In this operation, the lettuce seeds were coated with the present coating material 13. Air of 25° C. was blown for 30 minutes to the seeds coated with the present coating material 13, then, the seeds were dried overnight in a drying machine of 35° C., to obtain coated seeds having an average particle diameter of 3.0 mm (hereinafter, referred to as the present coated seed 13).

The amount of clothianidin contained in the present coated seed 13 was 104 g per 1 kg of the coated seeds.

Production Example 14

Fifty (50) parts by weight of palygorskite, 18 parts by weight of calcium stearate and 32 parts by weight of the present thermosetting resin powder 3 were mixed. This mixture was stirred for 30 minutes to obtain a coating material (hereinafter, referred to as the present coating material 14).

The same operation as in Production Example 13 was carried out, excepting that the present coating material 14 was used instead of the present coating material 13, to obtain coated seeds having an average particle diameter of 3.0 mm (hereinafter, referred to as the present coated seed 14).

The amount of clothianidin contained in the present coated seed 14 is 104 g per 1 kg of the coated seeds.

Production Example 15

Seventy six (76) parts by weight of palygorskite, 18 parts by weight of calcium stearate and 6 parts by weight of the present thermosetting resin powder 1 were mixed. This mixture was stirred for 30 minutes to obtain a coating material (hereinafter, referred to as the present coating material 15).

Eggplant seeds (80 g, number of seeds: about 20000) were rolled in a rolling granulator of centrifugal flow mode having a diameter of 36 cm. While spraying tap water onto the rolling seeds, 600 g of the present coating material 15 was gradually added. In this operation, the eggplant seeds were coated with the present coating material 15. Air of 25° C. was blown for 30 minutes to the seeds coated with the present coating material 15, further, the seeds were dried overnight in a drying machine of 35° C., to obtain coated seeds having an average particle diameter of 4.0 mm (hereinafter, referred to as the present coated seed 15).

The amount of clothianidin contained in the present coated seed 15 is 26 g per 1 kg of the coated seeds.

Production Example 16

Seventy four (74) parts by weight of palygorskite, 18 parts by weight of calcium stearate and 8 parts by weight of the present thermosetting resin powder 2 were mixed. This mixture was stirred for 30 minutes to obtain a coating material (hereinafter, referred to as the present coating material 16).

The same operation as in Production Example 15 was carried out, excepting that the present coating material 16 was used instead of the present coating material 15, to obtain coated seeds having an average particle diameter of 4.0 mm (hereinafter, referred to as the present coated seed 16).

The amount of clothianidin contained in the present coated seed 16 is 26 g per 1 kg of the coated seeds.

Production Example 17

Seventy three (73) parts by weight of palygorskite, 18 parts by weight of calcium stearate and 9 parts by weight of the present thermosetting resin powder 3 were mixed. This mixture was stirred for 30 minutes to obtain a coating material (hereinafter, referred to as the present coating material 17).

The same operation as in Production Example 15 was carried out, excepting that the present coating material 17 was used instead of the present coating material 15, to obtain coated seeds having an average particle diameter of 4.0 mm (hereinafter, referred to as the present coated seed 17).

The amount of clothianidin contained in the present coated seed 17 is 26 g per 1 kg of the coated seeds.

Reference Production Example 1

Thirty four (34) parts by weight of diatomaceous earth, 30 parts by weight of pyrophyllite, 11 parts by weight of sepiolite, 20 parts by weight of calcium stearate and 5 parts by weight of the present powdery pesticide 1 were mixed. This mixture was stirred for 30 minutes to obtain a coating material (hereinafter, referred to as reference coating material 1).

Cabbage seeds (63 g, number of seeds: about 20000) were rolled in a rolling granulator of centrifugal flow mode having a diameter of 36 cm. While spraying tap water onto the rolling seeds, a total amount of 340 g of the reference coating material 1 was gradually added. In this operation, the cabbage seeds were coated with the reference coating material 1. Air of 25° C. was blown for 30 minutes to the seeds coated with the reference coating material 1, further, the seeds were dried overnight in a drying machine of 35° C. to obtain coated seeds having an average particle diameter of 3.0 mm (hereinafter, referred to as reference coated seed 1).

The amount of clothianidin contained in the reference coated seed 1 is 25 g per 1 kg of the coated seeds.

Reference Production Example 2

Thirty one (31) parts by weight of diatomaceous earth, 28 parts by weight of pyrophyllite, 11 parts by weight of sepiolite, 20 parts by weight of calcium stearate and 10 parts by weight of the present powdery pesticide 1 were mixed. This mixture was stirred for 30 minutes to obtain a coating material (hereinafter, referred to as reference coating material 2).

The same operation as in Reference Production Example 1 was carried out, excepting that the reference coating material 2 was used instead of the reference coating material 1, to obtain coated seeds having an average particle diameter of 3.0 mm (hereinafter, referred to as the reference coated seed 2).

The amount of clothianidin contained in the reference coated seed 2 is 50 g per 1 kg of the coated seeds.

Reference Production Example 3

Cabbage seeds (63 g, number of seeds: about 20000) were rolled in a rolling granulator of centrifugal flow mode having a diameter of 36 cm. While spraying tap water onto the rolling seeds, 340 g of the reference coating material 2 was gradually added. In this operation, the cabbage seeds were coated with the reference coating material 2. Air of 25° C. was blown for 30 minutes to the seeds coated with the reference coating material, further, the seeds were dried overnight in a drying machine of 35° C. to obtain coated seeds having an average particle diameter of 3.0 mm (hereinafter, referred to as reference coated seed 3).

The amount of clothianidin contained in the reference coated seed 3 is 50 g per 1 kg of the coated seeds.

Reference Production Example 4

Thirty one (31) parts by weight of diatomaceous earth, 28 parts by weight of pyrophyllite, 10 parts by weight of sepiolite, 20 parts by weight of calcium stearate, 11 parts by weight of the present powdery pesticide 1 and 0.071 parts by weight of thiuram wettable powder (trade name: Sankyo Thiuram 80; manufactured by Hokkai Sankyo Co., Ltd.) were mixed. This mixture was stirred for 30 minutes to obtain a coating material (hereinafter, referred to as reference coating material 4).

The same operation as in Reference Production Example 3 was carried out, excepting that the reference coating material 3 was used instead of the reference coating material 2, to obtain coated seeds having an average particle diameter of 3.0 mm (hereinafter, referred to as the reference coated seed 4).

The amount of clothianidin contained in the reference coated seed 4 is 50 g per 1 kg of the coated seeds.

Reference Production Example 5

Sixty six (66) parts by weight of palygorskite, 18 parts by weight of calcium stearate and 16 parts by weight of the present powdery pesticide 1 were mixed. This mixture was stirred for 30 minutes to obtain a coating material (hereinafter, referred to as reference coating material 5).

Lettuce seeds 50 g (number of seeds: 37000) were rolled in a rolling granulator of centrifugal flow mode having a diameter of 36 cm. While spraying tap water onto the rolling seeds, 800 g of the reference coating material 5 was gradually added. In this operation, the cabbage seeds were coated with the reference coating material 5. Air of 25° C. was blown for 30 minutes to the seeds coated with the reference coating material 5, further, the seeds were dried overnight in the drying machine of 35° C. to obtain coated seeds having an average particle diameter of 3.0 mm (hereinafter, referred to as reference coated seed 5).

The amount of clothianidin contained in the reference coated seed 5 is 104 g per 1 kg of the coated seeds.

Reference Production Example 6

Seventy seven (77) parts by weight of palygorskite, 18 parts by weight of calcium stearate and 5 parts by weight of the present powdery pesticide 1 were mixed. This mixture was stirred to mix for 30 minutes to obtain a coating material (hereinafter, referred to as reference coating material 6).

Eggplant seeds (80 g, number of seeds: about 20000) were rolled in a rolling granulator of centrifugal flow mode having a diameter of 36 cm. While spraying tap water onto the rolling seeds, 600 g of the reference coating material 6 was gradually added. In this operation, the eggplant seeds were coated with the reference coating material 6. Air of 25° C. was blown for 30 minutes to the seeds coated with the reference coating material 6. Further, the seeds were dried overnight in a drying machine of 35° C. to obtain coated seeds having an average particle diameter of 4.0 mm (hereinafter, referred to as reference coated seed 6).

The amount of clothianidin contained in the reference coated seed 6 is 29 g per 1 kg of the coated seeds.

Test Example 1

A tray having 128 holes (8 columns×16 lines) of 3 cm×3 cm×4.5 cm (depth) was filled with a soil. Each one coated seed for test was sown with a depth of about 5 mm from the surface in each hole of this tray. This tray was supplied a sufficient amount of water. Thereafter, this tray was placed in a greenhouse of 25° C.

In this test, the present coated seed 4, the present coated seed 8 and the reference coated seed 2 were used.

After 35 days, leaf parts of the grown crops were observed. The extent of chemical injury was judged from the proportion of the yellowed area on leaf parts according to the following [evaluation criteria]. The ratio of chemically injured plants was calculated according to the following formula.

[Evaluation Criteria]

+++: the yellowed area on leaf parts is 5% or more based on the total leaf area

++: the yellowed area on leaf parts is 3% or more and less than 5% based on the total leaf area +: the yellowed area on leaf parts is 0% or more and less than 3% based on the total leaf area −: no yellowing on leaf parts Ratio of chemically injured plants (%)=(numbers of chemically injured plants/numbers of tested plants)×100

The results are shown in [Table 1].

TABLE 1

| Coated seed | Judgment | Ratio of chemically injured plants (%) |
|---|---|---|
| Present coated seed 4 | + | 3.3 |
| Present coated seed 8 | − | 0 |
| Reference coated seed 2 | +++ | 84.7 |

Test Example 2

A tray with 128 cells (8 columns×16 lines, cell size; 3 cm×3 cm×4.5 cm (depth)) was filled with a soil. Each one coated seed for test was sown with a depth of about 5 mm from the surface in each hole of this tray. This tray was supplied with a sufficient amount of water. Thereafter, this tray was placed in a greenhouse of 25° C.

In this test, the present coated seed 16, the present coated seed 17 and the reference coated seed 6 were used.

After 15 days, leaf parts of the grown crops were observed.

The results were evaluated according to the criteria described in Test Example 1.

The results are shown in [Table 2].

TABLE 2

| Coated seed | Judgment | Ratio of chemically injured plants (%) |
|---|---|---|
| Present coated seed 16 | + | 9.7 |
| Present coated seed 17 | − | 0 |
| Reference coated seed 6 | +++ | 58.8 |

Test Example 3

A tray with 128 cells (8 columns×16 lines, cell size; 3 cm×3 cm×4.5 cm (depth)) was filled with a soil. Each one coated seed for test was sown with a depth of about 5 mm from the surface in each hole of this tray. This tray was supplied with a sufficient amount of water. Thereafter, this tray was placed in a greenhouse of 25° C.

In this test, the present coated seed 9, the present coated seed 11 and the reference coated seed 3 were used.

After 29 days, leaf parts of the grown crops were observed.

The results were evaluated according to the criteria described in Test Example 1.

The results are shown in [Table 3].

TABLE 3

| Coated seed | Evaluation | Ratio of chemically injured plants (%) |
|---|---|---|
| Present coated seed 9 | + | 10.0 |
| Present coated seed 11 | − | 0 |
| Reference coated seed 3 | ++ | 83.3 |

Test Example 4

A tray with 128 cells (8 columns×16 lines, cell size; 3 cm×3 cm×4.5 cm (depth)) was filled with a soil. Each one coated seed for test was sown with a depth of about 5 mm from the surface in each hole of this tray. This tray was provided with a soil with a thickness of 5 mm, and supplied with a sufficient amount of water. Thereafter, this tray was placed in a greenhouse of 25° C.

In this test, the present coated seed 5, the present coated seed 9, the present coated seed 11 and the present coated seed 12 were used.

After 21 days, aerial pats of five stocks of the crop were cut. The crops were placed in a polyethylene cup. Forty (40) second-instar larvae of *Putella xylostella* were released on this polyethylene cup. Five days after, the dead insect number was counted, and the insect mortality rate was calculated according to the following formula.

Insect mortality rate (%)=(numbers of dead insects/numbers of tested insects)×100

The results are shown in [Table 4].

TABLE 4

| Coated seed | Insect mortality rate (%) |
| --- | --- |
| Present coated seed 5 | 97.5 |
| Present coated seed 9 | 97.5 |
| Present coated seed 11 | 90.0 |
| Present coated seed 12 | 83.3 |

Test Example 5

A tray with 200 cells (10 columns×20 lines, cell size; 2.4 cm×2.4 cm×4.5 cm (depth)) was filled with a soil. Each one coated seed for test was sown with a depth of about 5 mm from the surface in each hole of this tray. This tray was supplied with a sufficient amount of water. Thereafter, this tray was placed in a vinyl house at 23° C. during daytime and at 18° C. during nighttime. This vinyl hose had an opened entrance.

In this test, the present coated seed 13 and the present coated seed 14 were used.

After 21 days, the insect damage in each tray by *Chromatomyia horticola* was investigated, and the control value was calculated according to the following formula.

Control value (%)=(1−*Tai*/*Cai*)×100

Letters in the formula represent the following meanings

Cai: insect-damaged number in observing non-treated district

Tai: insect-damaged number in observing treated district

The results are shown in [Table 5].

TABLE 5

| Coated seed | Control value (%) |
| --- | --- |
| Present coated seed 13 | 91.5 |
| Present coated seed 14 | 68.0 |

Test Example 6

A tray with 128 cells (8 columns×16 lines, cell size; 3 cm×3 cm×4.5 cm (depth)) was filled with a soil. Each one coated seed for test was sown with a depth of about 5 mm from the surface in each hole of this tray. This tray was supplied a sufficient amount of water. Thereafter, this tray was placed in a greenhouse of 25° C.

In this test, the present coated seed 16 and the present coated seed 17 were used.

After 34 days, the grown crops were transplanted into a plastic cup (diameter 8.0 cm×height 7.0 cm) filled with a soil. Sixty two (62) days after sowing, adult insects and larvae of *Frankliniella occidentalis* were released at a rate of an average of 7.4 per stock. Further, the crops were allowed to stand for 15 days at 23 to 25° C. Thereafter, the survived insect number was checked, and the control value was calculated according to the following formula.

Control value (%)=(1−*Tai*/*Cai*)×100

Letters in the formula represent the following meanings

Cai: survived insect number in observing non-treated district

Tai: survived insect number in observing treated district

The results are shown in [Table 6].

TABLE 6

| Coated seed | Average numbers of individuals | Control value (%) |
| --- | --- | --- |
| Present coated seed 16 | 1.0 | 87.9 |
| Present coated seed 17 | 2.5 | 69.7 |

Test Example 7

A tray with 128 cells (8 columns×16 lines, cell size; 3 cm×3 cm×4.5 cm (depth)) was filled with a soil. Each one coated seed for test was sown with a depth of about 5 mm from the surface in each hole of this tray. This tray was supplied with a sufficient amount of water. Thereafter, this tray was placed in a greenhouse (average temperature; daytime: 28° C., nighttime: 23° C.)

In this test, the present coated seed 6, the present coated seed 10 and the reference coated seed 4 were used.

After 8 days, leaf parts of the grown crops were observed. The results were evaluated according to the criteria described in Test Example 1.

The results are shown in [Table 7]

TABLE 7

| Coated seed | Evaluation | Ratio of chemically injured plants (%) |
| --- | --- | --- |
| Present coated seed 6 | ++ | 62.5 |
| Present coated seed 10 | + | 18.7 |
| Reference coated seed 4 | +++ | 87.5 |

Test Example 8

A tray with 128 cells (8 columns×16 lines, cell size; 3 cm×3 cm×4.5 cm (depth)) was filled with a soil. Each one coated seed for test was sown with a depth of about 5 mm from the surface in each hole of this tray. This tray was supplied with a sufficient amount of water. Thereafter, this tray was placed in a greenhouse (average temperature; daytime: 28° C., nighttime: 23° C.)

In this test, the present coated seed 6, the present coated seed 10 and the reference coated seed 4 were used.

After 8 days, aerial pats of fifteen stocks of the crop were cut. The crops were placed in a polyethylene cup. Thirty (30) second-instar larvae of *Spodoptera litura* were released on this polyethylene cup. Three days after, the numbers of dead insects was counted, and the insect mortality rate was calculated according to the following formula.

Insect mortality rate (%)=(numbers of dead insects/numbers of tested insects)×100

The results are shown in [Table 8].

TABLE 8

| Coated seed | Insect mortality rate (%) |
| --- | --- |
| Present coated seed 6 | 76.7 |
| Present coated seed 10 | 83.3 |
| Reference coated seed 4 | 66.7 |

INDUSTRIAL APPLICABILITY

The coated seed of the present invention is suitable for protecting agricultural crops by damages of diseases and pests.

The invention claimed is:

1. A coated seed comprising a seed and a coating material comprising an inorganic mineral powder and a thermosetting resin powder, wherein the amount of the coating material is 3 to 200 kg based on 1 kg of the seed, the thermosetting resin powder has an average particle diameter of 10 to 200 μm and is obtained by aggregating a powdery pesticide with a thermosetting resin, and the powdery pesticide comprises an amount of pesticidally active component that is effective to protect a crop germinated from the seed against a disease or pest without causing significant chemical injury to the crop.

2. The coated seed according to claim 1, having an average particle diameter of 1 to 20 mm.

3. The coated seed according to claim 1, wherein the coating material comprises 10 to 99.5 wt % of the inorganic mineral powder and 0.5 to 90 wt % of the thermosetting resin powder.

4. The coated seed according to claim 3, wherein the coating material further comprises 5 to 30 wt % of a water repellent agent.

5. The coated seed according to claim 1, wherein the thermosetting resin powder comprises 10 to 90 wt % of the pesticidally active component.

6. The coated seed according to claim 5, wherein the thermosetting resin is a urethane resin.

7. The coated seed according to claim 1, wherein the amount of the pesticidally active component in 1 kg of the coating seed is 5 to 200 g.

8. The coated seed according to claim 1, wherein the powdery pesticide comprises clothianidin.

9. The coated seed according to claim 1, wherein the seed is a seed of genus *Brassica* crops, genus *Lactuca* crops or *Solanaceous* crops.

10. The coated seed according to claim 1, wherein the seed is a long-shaped seed.

11. The coated seed according to claim 1, wherein the seed is a seed having a particle diameter of 1.0 to 4.0 mm.

12. The coated seed according to claim 2, wherein the coating material comprises 10 to 99.5 wt % of an inorganic mineral powder and 0.5 to 90 wt % of a thermosetting resin powder.

13. The coated seed according to claim 12, wherein the coating material further comprises 5 to 30 wt % of a water repellent agent.

14. The coated seed according to claim 1, wherein the thermosetting resin powder is obtained by a procedure comprising:
 (a) mixing the powdery pesticide with a first liquid component to obtain a mixture, wherein the first liquid component comprises a first raw material of the thermosetting resin;
 (b) adding a second liquid component to the mixture, wherein the second liquid component comprises a second raw material of the thermosetting resin;
 (c) allowing the first liquid component to react with the second liquid component to generate the thermosetting resin, thereby obtaining a powdery pesticide thermosetting resin solidified material; and
 (d) further adding the first liquid component and the second liquid component to the powdery pesticide thermosetting resin solidified material to coat the material with the thermosetting resin, thereby obtaining the thermosetting resin powder.

15. The coated seed according to claim 1, wherein the coating material further comprises calcium stearate.

16. The coated seed of claim 1, wherein the thermosetting resin is selected from the group consisting of a urethane resin, a urea resin, a urethane-urea resin, and an epoxy resin.

* * * * *